(12) United States Patent
Chen

(10) Patent No.: US 11,359,227 B2
(45) Date of Patent: Jun. 14, 2022

(54) GENOME-WIDE MAPPING OF DNA-DNA PROXIMITIES IN THE NUCLEUS

(71) Applicant: University of Southern California, Los Angeles, CA (US)

(72) Inventor: Lin Chen, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 420 days.

(21) Appl. No.: 16/467,941

(22) PCT Filed: Dec. 8, 2017

(86) PCT No.: PCT/US2017/065418
§ 371 (c)(1),
(2) Date: Jun. 7, 2019

(87) PCT Pub. No.: WO2018/107093
PCT Pub. Date: Jun. 14, 2018

(65) Prior Publication Data
US 2020/0071746 A1 Mar. 5, 2020

Related U.S. Application Data

(60) Provisional application No. 62/432,523, filed on Dec. 9, 2016.

(51) Int. Cl.
| | |
|---|---|
| *C12P 19/34* | (2006.01) |
| *C12Q 1/6806* | (2018.01) |
| *G16B 15/00* | (2019.01) |
| *A01N 1/02* | (2006.01) |
| *C12Q 1/6869* | (2018.01) |

(52) U.S. Cl.
CPC ......... *C12Q 1/6806* (2013.01); *A01N 1/0284* (2013.01); *C12Q 1/6869* (2013.01); *G16B 15/00* (2019.02)

(58) Field of Classification Search
CPC .............................. C12Q 1/6806; C12Q 1/6869
See application file for complete search history.

(56) References Cited

U.S. PATENT DOCUMENTS

| | | | |
|---|---|---|---|
| 2010/0081141 A1* | 4/2010 | Chen ................ | C12Q 2523/101 435/6.1 |
| 2011/0287947 A1 | 11/2011 | Chen et al. | |
| 2014/0315762 A1* | 10/2014 | Keefe ................... | C12N 15/10 506/26 |

OTHER PUBLICATIONS

El-Sagheer and Brown, "Click Nucleic Acid Ligation: Applications in Biology and Nanotechnology," *Acc. Chem. Res.* (2012), 45(8):1258-1267, American Chemical Society.
Elsner et al., "Photochemical Crosslinking of Protein and DNA in Chromatin," *Anal. Biochem.* (1985), 149(2):575-581, Academic Press, Inc.
Oeffinger et al., "Comprehensive Analysis of Diverse Ribonucleoprotein Complexes," *Nature Methods* (2007), 4(11):951-956, Nature Publishing Group.

* cited by examiner

*Primary Examiner* — Kenneth R Horlick
(74) *Attorney, Agent, or Firm* — DLA Piper LLP (US)

(57) ABSTRACT

Disclosed are methods and systems for determining the three-dimensional structure of chromatin in eukaryotic cells. More specifically, disclosed are methods and systems for obtaining chromatin structural information by surface immobilization that includes tethering crosslinked protein:DNA complexes and/or ligated DNA complexes to media such as beads, gels, and or matrices during the conformation capture assay. In general, the method includes flash freezing a cell such that the structural organization of the chromatin or other protein:DNA complexes is preserved, cryomilling the cell, producing cross-linked protein:DNA complexes by cutting the chromatin using a chemical, physical or enzymatic method, substantially immobilizing the cross-linked protein:DNA complexes, ligating the cross-linked protein:DNA complexes intramolecularly such that the ligated protein:DNA complexes represent structural organization of the chromatin; characterizing the ligated DNA by sequencing or other methods; and identifying any structural organization of the chromatin. The structural organization preferably includes information relating to interacting loci of the chromatin.

15 Claims, 13 Drawing Sheets a    5'- azide to 3'- propargyl click ligation b    3'- azide to 5'- propargyl click ligation

FIGURE 11

| | Stats of the PE 150 seq data | |
|---|---|---|
| Total pairs | 14,108,063 | 100% |
| Valid contacts | 2,722,562 | 19.3% |
| Single end | 1,777,891 | 12.6% |
| Dangling end | 488,045 | 3.5% |
| Religation | 4,662,097 | 33% |
| junk | 4,457,468 | 31.6% |

GENOME-WIDE MAPPING OF DNA-DNA PROXIMITIES IN THE NUCLEUS

CROSS-REFERENCE TO RELATED APPLICATIONS

This application is a 35 USC § 371 National Stage application of International Application No. PCT/US2017/065418 filed Dec. 8, 2017, now pending; which claims the benefit under 35 USC § 119(e) to U.S. Application Ser. No. 62/432,523 filed Dec. 9, 2016. The disclosure of each of the prior applications is considered part of and is incorporated by reference in the disclosure of this application.

STATEMENT REGARDING FEDERALLY SPONSORED RESEARCH AND DEVELOPMENT

This invention was made with government support under Grant Nos. R01 GM064642, R01 AI113009-01 A1 and 5U54 DK107981 awarded by the National Institutes of Health. The government has certain rights in the invention.

FIELD OF THE INVENTION

The present invention relates to methods and systems for determining the three-dimensional structure of chromatin in eukaryotic cells.

BACKGROUND OF THE INVENTION

Imaging analyses have long established that the 3D structure of the nucleus and its dynamic nature are closely related to cellular functions. However, it is not until recently that genome-wide analyses of the nuclear structure start to reach molecular level. Preliminary studies suggest that direct physical models of the genome can be generated from extensive mapping of chromatin interactions and population-based modeling and that the resulting models can yield insights about genomic functions via statistical analyses. While these studies provide a glimpse of the great potential of understanding cellular functions from the molecular structures of the nucleus, it remains a major challenge to develop an accurate physical model of the nucleus in space and time and relate the model structures to cellular functions. Thus, there is a need to develop comprehensive and robust approaches to structural analyses of the nucleus.

Based on the pioneering work of chromosome conformation capture by Dekker et al. [Dekker, Science 2002], the inventors have independently developed a Genome-wide Chromosome Conformation capture strategy (see e.g., WO 2011/146056; U.S. Pat. No. 8,076,070; Kalhor et al., Nat Biotech 2011) and further refined the experimental protocol by tethering the cross linked chromatin complexes on solid surfaces, known as tethered conformation capture (TCC). Although TCC is similar in principle to the more widely known, solution-based HiC protocol [Science 2009], immobilization of chromatin complexes on low density surfaces eliminates excess free DNA and reduces intermolecular ligations, thus greatly enhancing signal-to-noise ratio and improving data quality. Preliminary studies have shown that these improvements are critical to accurate measurements of inter-chromosomal interactions which are generally of low frequency and yet essential to faithfully model the overall genome structures. Moreover, solid phase immobilization also facilitates many subsequent chemical and enzymatic steps that require different reaction conditions and buffers, paving the way for the present invention.

DNA offers a number of advantages for structural analysis of the nucleus at the molecular level, which have been demonstrated in preliminary studies by others and the inventors in the development and application of HiC and TCC.

To derive structural information about genome, the inventors developed a method similar to the genome-wide chromosome conformation capture technique (termed Hi-C) described by Lieberman-Aiden et al. However, in preliminary studies with human GM12878 lymphoblastoid cells, the inventors found that solution-based chromosome conformation capture techniques contain a high background of random inter-molecular ligations between DNA fragments not cross-linked together [see FIG. 2c of Kalhor et al.], which leads to false chromatin contacts. These false contacts were particularly detrimental to inter-chromosomal contact measurement [see FIG. 2d,e of Kalhor et al] and could severely hinder structure calculations of large genomes. To overcome this problem, the inventors developed a tethered conformation capture technology (TCC) for mapping chromatin interactions (FIG. 1). In contrast to Hi-C, key reactions in TCC are carried out on solid phase, so the large excess of free DNA is washed away and the immobilized protein-DNA complexes cannot diffuse freely, both effectively reduce random inter-molecular ligations. The inventors have shown that TCC has much higher signal-to-noise ratios that enhance the accuracy of contact measurements within and between chromosomes. The most significant advantage of TCC is that multiple steps of a given chromosome conformation capture protocol can be carried out on solid phases, which facilitate buffer solution exchange and implementation of various experimental strategies to improve efficiency and signal-to-noise ratio, and possible automation. The present invention optimizes deficiencies in various steps outlined in FIG. 1.

SUMMARY OF THE INVENTION

It is one object of the present invention to provide methods and systems for the determination of 3-dimensional chromatin structure at higher resolutions and with less noise.

It is another object of the present invention to provide methods and systems for the determination of 3-dimensional chromatin structure at a specific time point.

It is another object of the present invention to provide methods and systems of genome-wide conformation capture which substantially eliminate intermolecular ligation during the conformation capture technique.

Another object of the present invention is to provide a new approach for high-throughput genome-wide analysis of 3D organization of chromatin having high resolution and low noise. This approach significantly reduces experimental noise by using surface immobilization rather than dilution for promoting intramolecular ligations. Surface immobilization makes possible more powerful analysis of global 3D arrangement of the genome and higher resolution evaluation of local chromatin conformation.

It is one discovery of the present invention that surface-immobilization of complexes, in contrast to reducing the concentration, effectively diminishes ligation between complexes. This renders conformation capture more effective by dramatically increasing the signal to noise ratio. Surface immobilization also enables more intricate modifications being carried out on cross-linked chromatin. Additionally, it paves the way for automation of such reactions.

One embodiment of the present invention is a method directed to a genome-wide conformation capture method of determining the three-dimensional arrangement of chromatin in a cell or a population of cells in tissues and organs. The method includes flash freezing a cell such that the structural organization of the chromatin or other protein:DNA complexes is preserved, cryomilling the cell, producing cross-linked protein:DNA complexes by cutting the chromatin using a chemical, physical or enzymatic method, substantially immobilizing the cross-linked protein:DNA complexes, connecting the cross-linked protein:DNA complexes intramolecularly such that the connected protein:DNA complexes represent structural organization of the chromatin; characterizing the connected DNA by sequencing or other methods; and identifying any structural organization of the chromatin. Preferably, the sequencing is massively parallel or ultra-high throughput sequencing. The structural organization preferably includes information relating to interacting loci of the chromatin.

In another embodiment, the connecting step includes click DNA ligation.

In another embodiment, the chromatin is denatured.

In a further preferred embodiment of the present invention, the protein:DNA complexes are cut by restriction digestion. Preferably, the chromatin is digested with a restriction enzyme that produces a 5' overhang of at least two non-identical bases, and the 5' overhang is subsequently blunted. In one embodiment, blunting may be done with nucleotide analogues, and more preferably, a biotinylated nucleotide and nuclease resistant nucleotide is used for blunting. Preferably, a 2-deoxy-nucleoside-5'-(alpha-thio)-triphosphate is used in blunting.

In connection with the preferred embodiment of the present invention, the protein:DNA complexes are substantially immobilized by tethering the protein:DNA complexes to one or more media. The media may be one or more media that includes beads, chips, colloids, matrices, and gels, and the protein:DNA complexes may be tethered on the surface of or on the inside of the media. In a preferred embodiment, the protein:DNA complexes are substantially immobilized by a noncovalent or covalent bond between the side-chains of the amino acids of the proteins of chromatin and a reactive chemical group on the surface or inside of one or more media that includes beads, chip, colloids, matrix, and gel. It is noted that streptavidin-biotin bonding is not covalent, nevertheless the bonding is very strong.

In a further preferred embodiment of the present invention, the protein:DNA complexes are substantially immobilized by modifying the proteins of the chromatin so as to tether/anchor the modified protein:DNA complexes to the surface or inside of one or more media that includes beads, colloids, matrices, and gels. In connection with this embodiment, the protein:DNA complexes may be substantially immobilized by biotinylating the proteins of the chromatin so to tether the biotinylated protein:DNA complexes to the biotin binding surfaces such as streptavidin-coated surfaces that includes but are not limited to chips and beads. Instead of streptavidin itself, variations such as avidin and neutravidin can be used. The thiol groups of the proteins, including the thiol groups of cysteine residues, may be biotinylated so as to tether/anchor the biotinylated protein:DNA complexes to streptavidin, avidin or neutravidin coated surfaces (i.e., biotin binding surfaces).

Alternatively, the protein:DNA complexes may be substantially immobilized by biotinylating the N-termini and lysine residues of the proteins of the chromatin so to tether the biotinylated protein:DNA complexes to streptavidin coated chips or beads. Or the protein:DNA complexes may be substantially immobilized by biotinylating the glutamate or aspartate residues of the proteins of the chromatin so to anchor the biotinylated protein:DNA complexes to streptavidin or related coated chips or beads.

In another embodiment, the protein:DNA complexes are substantially immobilized through modifying the proteins of the chromatin so as to anchor the modified protein:DNA complexes to the surface or inside of one or more media that include beads, colloids, matrix, and gel.

In another embodiment, the protein:DNA complexes are substantially immobilized by biotinylating the proteins of the chromatin so as to anchor the biotinylated protein:DNA complexes to a biotin binding surface.

In another embodiment, the protein:DNA complexes are substantially immobilized by biotinylating the thiol groups of the proteins of the chromatin so as to anchor the biotinylated protein:DNA complexes to a biotin binding surface.

In another embodiment, the protein:DNA complexes are substantially immobilized by biotinylating the cysteine residues of the proteins of the chromatin so as to anchor the biotinylated protein:DNA complexes to a biotin binding surface.

In another embodiment, the protein:DNA complexes are substantially immobilized by biotinylating the N-termini and lysine residues of the proteins of the chromatin so as to anchor the biotinylated protein:DNA complexes to a biotin binding surface.

In another embodiment, the protein:DNA complexes are substantially immobilized by biotinylating the glutamate or aspartate residues of the proteins of the chromatin so as to anchor the biotinylated protein:DNA complexes to a biotin binding surface.

In another embodiment, thiol groups are added to the proteins of chromatin through a chemical reagent.

In another embodiment, thiol groups are added to the proteins of chromatin through reacting the proteins of chromatin with an aminothiol and a crosslinking reagent.

In another embodiment, thiol groups are added to the lysines of the proteins of chromatin by reacting them with a cross-linking reagent and cysteamine.

In another embodiment, thiol groups are added to the lysines of the proteins of chromatin by reacting them with formaldehyde and cysteamine.

In another embodiment, the surface is streptavidin-coated chips or magnetic beads.

In another embodiment, the cells are denatured with sodium dodecyl sulfate.

In another embodiment, the chromatin is digested with a restriction enzyme that produces a 5' overhang of at least two non-identical bases.

In another embodiment, the 5' overhang is blunted.

In another embodiment, the connection of the protein:DNA complexes intramolecularly is done by blunt-ended ligation using DNA ligase.

In another embodiment, the blunting is done with nucleotide analogues.

In another embodiment, a biotinylated nucleotide is used for blunting.

In another embodiment, a nuclease resistant nucleotide analogue is used in blunting.

In another embodiment, a 2-deoxy-nucleoside-5'-(alpha-thio)-triphosphate is used in blunting.

In another embodiment, after the connecting step, protein:DNA complexes that have not undergone connection are removed.

In another embodiment, the sequencing is massively parallel or ultrahigh-throughput sequencing.

In another embodiment, the structural organization is interacting loci in the nucleus of the cell.

In a further embodiment of the present invention, thiol groups are added to the proteins of chromatin through a chemical reagent. The thiol groups may be added to the proteins of chromatin through reacting the proteins of chromatin with an aminothiol and a crosslinking reagent. The thiol groups may be added to the lysines and N-termini of the proteins of chromatin by reacting them with a cross-linking reagent and cysteamine, for instance, by reacting them with formaldehyde and cysteamine.

Preferably, ends of cross-linked protein:DNA complexes are connected intramolecularly by ligation, and more preferably by blunt-ended ligation using DNA ligase. After the ligating step, protein:DNA complexes that have not undergone ligation are preferably removed.

Another embodiment of the present invention is directed to a tethered conformation capture method in which cross-linked protein-DNA complexes are immobilized on a surface where most reactions take place. According to this method, cells are crosslinked with formaldehyde and treated with Iodoacetyl-PEG2-Biotin to biotinylate the cysteine residues of all proteins. Chromatin is then digested with a restriction enzyme that leaves 5' overhangs. After digestion, crosslinked protein-DNA complexes are immobilized on the surface of streptavidin-coated magnetic beads through biotinylated proteins and excess streptavidin is blocked. 5' overhangs are filled in with an α-thio-triphosphate containing nucleotide analogue inserted before a biotinylated nucleotide. Blunt DNA ends are then ligated while immobilization prevents free diffusion of the complexes and therefore promotes intramolecular ligations. After ligation, DNA is purified which separates it from the surface and crosslinked proteins. The biotinylated nucleotides on DNA ends that have not participated in ligation are then removed using *E. coli* Exonuclease III (ExoIII). ExoIII catalyzes removal of mononucleotides from 3'-hydroxyl termini of duplex DNA until it encounters the exonuclease resistant phosphorothioate bond, which is inserted on the 5' of the biotinylated nucleotide by incorporation of the α-thio-triphosphate containing nucleotide. After exonuclease treatment, DNA is sheared and the fragments that include a ligation junction and have therefore maintained biotin, are isolated on streptavidin-coated magnetic beads. A library is prepared of these fragments and is sequenced from both ends on an ultra-high throughput sequencing platform, generating a binary contact profile that contains millions of potential interactions.

Another embodiment of the present invention is an improved method for determination of the structural organization of chromatin having less noise and higher resolution. The improved method includes providing chromatin having DNA cross-linked to protein such that the structural organization of the chromatin is preserved, producing cross-linked protein:DNA complexes by cutting the chromatin with a restriction enzyme; substantially immobilizing the cross-linked protein:DNA complexes on a surface and removing non-crosslinked DNA generated by digesting the chromatin, ligating the cross-linked protein:DNA complexes intramolecularly and removing DNA molecules without a ligation junction, preferably by washing. Preferably, the chromatin is digested with a restriction enzyme that produces a 5' overhang of at least two non-identical bases. Preferably, the method includes sequencing the DNA of the ligated/connected protein:DNA complexes.

The immobilizing of the cross-linked protein:DNA complexes reduces the frequency of intermolecular ligations during the ligation. Preferably, the protein:DNA complexes are substantially immobilized by tethering the protein:DNA complexes on the surface of one or more media selected that include beads, matrix, and gel. Preferably, DNA molecules without a ligation junction are removed by an exonuclease and washing.

In another embodiment, immobilizing the cross-linked protein:DNA complexes reduces the frequency of formation of inter-molecular connections.

In another embodiment, DNA molecules without a connection junction are removed by an exonuclease.

In another embodiment, protein:DNA complexes are substantially immobilized by a covalent or non-covalent bond between the DNA of chromatin and a reactive chemical group on the surface or inside of one or more media that includes beads, chip, colloids, matrix, and gel.

In another embodiment, connection of the DNA of the crosslinked protein:DNA complexes intramolecularly is done by ligation using DNA ligase.

In another embodiment, the protein:DNA complexes are substantially immobilized relative to each other.

Most current mapping technologies (HiC or TCC, ChIA-PET etc) depend on formaldehyde cross-linking to capture DNA proximity information through covalently cross-linked higher-order protein-DNA complexes. To overcome the limitation of formaldehyde cross-linking and provide direct structural information based on DNA-DNA proximities, the present invention uses photo cross-linking technologies to directly probe DNA proximity information. These technologies and probes have high efficiency, regioselectivity, and temporal resolution that are capable of dynamic analysis of genome organization of single cells as well as ensemble population of cells. Moreover, coupled with imaging methods, the probes can be used to target selected regions of interest in the nucleus. For example, using GFP tagged proteins, regions of transcription active regions in the nucleus, known as transcription factory, can be located and UV can be used to focus on selected factory locus to find out what DNA are at or near at the illuminated transcription factory.

Another embodiment of the present invention is directed to a method of determining the three-dimensional arrangement of chromatin in a cell or tissue. The method uses photo-crosslinking to capture DNA-DNA proximity information in a cell.

The method involves the design of bi-functional photo crosslinking probes that bind and/or intercalate DNA at both ends, and under illumination by long wavelength UV or UV laser (e.g., ~360 nm), form a covalent adduct with DNA, thereby crosslinking two double stranded DNA in close spatial proximity together.

The photo cross-linking probes are cell permeable and bind DNA throughout the genome in a live nucleus. The probes have no or low cellular toxicity and do not significantly interfere with cellular/nuclear activities, at least during the short incubation time (for diffusion and binding). Many dye molecules used for nuclear staining of live cells meet these criteria. The photochemical crosslinking can be initiated at any given time point of the cell cycle. To achieve temporal resolution, UV laser of long wavelength can be used to activate photoaffinity labeling groups in seconds to capture the structure of the genome structure in a well-defined time point. So literally a UV picture of the DNA skeleton is taken in the nucleus and can be detected using biochemical approaches to extract structural information such as TCC and related protocols.

At least three classes of probe design can be used. The first one is based on natural products that bind/intercalate DNA, have intrinsic photo cross-linking activity (e.g., Psoralen) and can be crosslinked to DNA with high efficiency under illumination with UV laser. The second one is based on well-established DNA staining molecules (e.g., Hoechst dye and DAPI) that are cell permeable, have low cellular toxicity and bind DNA in a largely non-specific manner. Using these DNA-binding dye molecules as a template, photoaffinity labeling groups (such as azido and diazirine) at appropriate positions that do not interfere with DNA binding but have enhanced photo crosslinking efficiency by being close to the aromatic ring of DNA bases can be introduced by custom synthesis. The third one is based on polyamides than can be designed to bind specific DNA target sequences. Again photoaffinity labeling groups (such as azido and diazirine) can be introduced to appropriate positions on polyamides without interfering with DNA binding and with enhanced photo crosslinking efficiency by being close to DNA bases.

Chimeric probes using combinations of different classes of molecules described above. Based on the differences of DNA binding preference of psoralen, DAPI/Hoechst 33258 and polyamides can be made. These homo or hetero bi-functional photo crosslinking probes can be used to capture DNA-DNA contacts globally or for selected regions.

The linker that connects the two photo-crosslinking probes can be designed for various applications. Different types of linkers (e.g., simple alkane chain, polyethylene glycol-PEG etc.) can be used. The linker can be synthetically engineered to have different lengths and rigidities, which can be used to probe structural information at various length scales.

The linker can also be engineered to bear affinity tags that can facilitate the purification and enrichment of photo-crosslinked DNA fragments.

Specifically, an alkyne can be introduced into the linker that can be used to react with biotin-linked azide through click chemistry for the purification of photo crosslinked DNA. The bi-functional photo-crosslinking probes can be used to capture DNA-DNA contacts in the cells using a variety of chromosome conformation capture protocols. The following describes a work flow based on the inventor's previously established tethered conformation capture (TCC) platform:

First, the bi-functional photo-crosslinking probes will be incubated with cells for a few minutes to allow diffusion of the probes into the nucleus and the binding of probes to genome DNA.

Then the cells will be illuminated by long wavelength UV (330-370 nm) to activate the probes that covalently crosslink DNA (and RNA if they are nearby). If a UV laser that can deliver a high dose of photons per second is used, the photo crosslinking can be complete in seconds, thereby capturing the genome structure in a well-defined time point and state. Moreover, a focused UV laser can be used to illuminate a given region in the cells or the nucleus and identify genome sequences in that region at a specific time in addition to the DNA-DNA proximities information in the same region.

Next, the genomic DNA will be extracted from the cells using standard protocols. This step will be very different from the formaldehyde crosslinking-based 3C/HiC/TCC protocols because the chromosome structure is no longer needed to be kept intact under mild conditions, as required by the formaldehyde-based 3C/HiC/TCC protocols. This is because the DNA-DNA proximity information has already been preserved in the photo crosslinking step in situ. As a result, cell lysis and DNA extraction can be done with much harsher conditions to ensure maximum recovery, thereby increasing the data acquisition efficiency in mapping genome-wide DNA-DNA contacts.

Then, the purified genome DNA can be digested by a chosen restriction enzyme. Again, in contrast to the formaldehyde crosslinking-based 3C/HiC/TCC protocols, this step is performed with purified and naked DNA. Without bound nucleosomes and other nuclear proteins and the need to maintain DNA in the crowded genomic environment, the restriction digestion should be much more efficient and less biased by genomic contexts, because the recovered chromosomal DNA is fully naked and all the restriction sites throughout the genome should be equally accessible to the digestion enzymes, thereby reducing potential bias inherently associated with the original HiC/TCC protocols. The enhanced access of restriction enzymes to genome DNA sites should also increase the data acquisition efficiency in mapping genome-wide DNA-DNA contacts.

Next, the digested DNA mixture will be reacted with biotin-linked azide. Since the probe contains an alkyne in the linker region, DNA-DNA junction crosslinked to the probe can be purified and enriched by click reaction using magnetic beads coated with streptavidin.

The DNA-DNA complex tethered onto the streptavidin magnetic beads can then be processed as the TCC protocols for sequencing. Briefly, the DNA ends can be filled in with biotin-labeled base and joined by ligation. Again, the ligation efficiency with purified and naked DNA should be much higher than the formaldehyde crosslinking-based 3C/HiC/TCC protocols because the ligation is now done without bound nucleosomes and the need to maintain DNA-DNA proximities by formaldehyde crosslinked higher-order nuclear protein complexes. The resulting DNA can be sheared to small fragments and the ligation junction can be enriched by another round of streptavidin magnetic beads pull-down. The recovered DNA can be prepared (end repair and adaptor attachment) for sequencing.

Other aspects and advantages of the invention will be apparent from the following description and the appended claims.

BRIEF DESCRIPTION OF THE DRAWINGS

FIG. 6a Design of psoralen-based bifunctional DNA-DNA Photo cross-linking to probes. (Top) The crystal structure of psoralen bound to DNA, the structure shown is the monoadduct (pdb code 203D.pdb); The exposed atoms of psoralen (indicated by arrow) are potential linker sites; (Bottom) one example of the designed probe with indicated features: two types of linker with variable lengths, a cleavable linker, a alkyne group for click reaction to biotin linked azide for affinity purification. FIG. 6b. Synthetic scheme for one psoralen based bi-functional photo crosslinking probe.

FIG. 7a Design of DAPI-based bifunctional DNA-DNA Photo cross-linking to probes. (Left) The crystal structure of DAPI bound to DNA (pdb code 1D30.pdb); (Right top) Modification sites on DAPI; (Right bottom): a sketch of a DAPI-based probe, the linker is similar to that shown in FIG. 6 and not shown. FIG. 7b. Design of Hoechst 33258-based bifunctional DNA-DNA Photo cross-linking to probes. (Left) The structure of Hoechst 33258 bound to DNA; (Right top) Modification sites on Hoechst 33258; (Right bottom): a sketch of a Hoechst 33258-based probe, the linker is similar to that shown in FIGS. 2 and 3. Examples of photoaffinity labeling groups are shown to the right.

FIG. 11. The Pair End 150 sequencing data testified to the probe's bis-tethering function by examining the RE new ligated sequence (20%). The 2D genome map showed an entirely different chromatin contacts pattern. Since the initial probe is of fixed length and can only tether the DNAs out once planarly intercalated on both strands, the data presents a DNA loop contacts in the genomic open region.

DETAILED DESCRIPTION OF THE INVENTION

Figure 1:
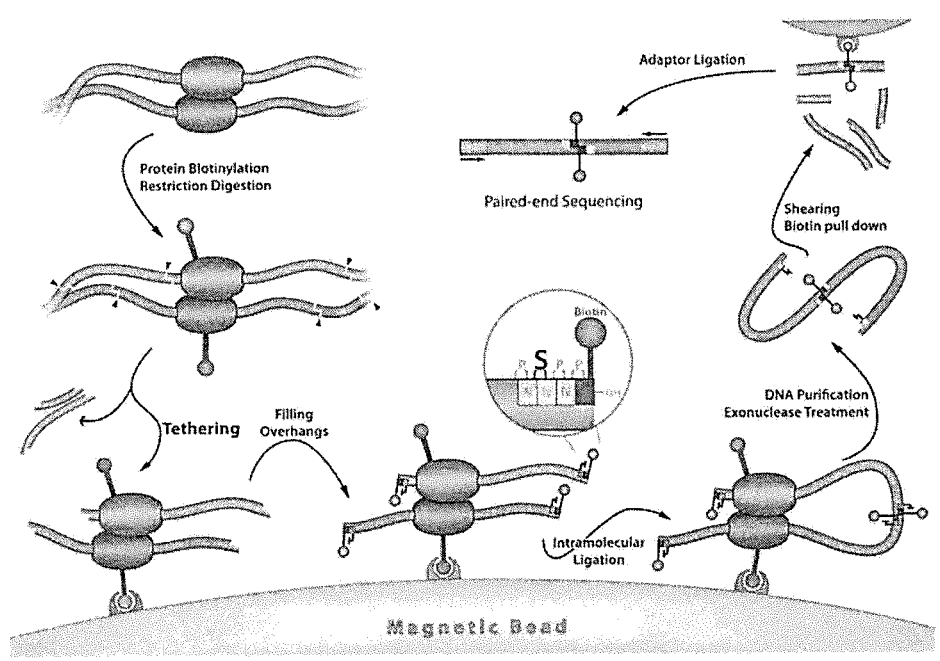
FIG. 1. Detecting genome-wide chromatin contacts using tethered conformation capture (TCC) The native chromatin contacts were preserved by chemically cross-linking DNA and proteins. The DNA was then digested with a restriction enzyme, and, after cysteine biotinylation of proteins, the protein-bound fragments were immobilized at a low surface density on streptavidin-coated beads. The immobilized DNA fragments were then ligated while tethered to the surface of the beads. Finally, ligation junctions were purified, and ligation events were detected by massively parallel sequencing, a process that revealed the genomic locations of the pairs of loci that had formed the initial contacts.

A major limitation of the current HiC/TCC protocol is the low data acquisition efficiency. It is estimated that only a few thousands of DNA-DNA proximity contacts can be detected per cell. Compared with the billion base-pair size of the genome of mammalian cells, this low data coverage presents severe problems in structural modeling due to the extremely low observation-to-parameter ratio and potential bias as some regions are over sampled whereas some other regions are under sampled. Several factors may contribute to the low data acquisition efficiency, including: (1) Low efficiency of the current method (chemical cross-linking by formaldehyde) to capture chromatin structure; (2) Limited efficiency in surface tethering; (3) Low efficiency in blunt end ligation after the incorporation of biotin-bearing base analogs into the DNA ends. Problem #2 is specific to the TCC protocol and solutions and is briefly addressed in the present invention. Problems #1 and #3 are significant issues impacting a wide range of protocols related to HiC and TCC. A major part of the present invention addresses these two issues. For problem #1, fundamentally different ways to preserve/capture chromatin interactions are adopted (refer to sections of "Adapting Cryomilling to HiC/TCC analysis" and "Photo cross-linking technologies to directly probe DNA proximity information"). For problem #3, the inventors developed ligation-free chemical approaches to link the two DNA strands representing the chromatin contact in 3D structure of the genome (see below). With regard to problem #2, the inventors initially used thiol-reacting biotin conjugating reagent to show that TCC can reduce noise. However, some chromatin complexes may be lost due to: (i) lack of surface exposed Cys residues; (ii) oxidation of surface Cys residues during previous steps; (iii) incomplete reaction of Cys with the iodoacetamide group. To address this problem, the inventors introduce additional tethering reagents that target Lys residues. By monitoring the total DNA recovered on the streptavidin beads from the same formaldehyde cross-linked/enzyme digested pool of chromatin complexes, the inventors can improve the tethering efficiency by testing different biotin conjugating reagents and combinations. Studies indicated that this approach can lead to better tethering efficiency.

Adapting Cryomilling to HiC/TCC Analysis

A major challenge in structural study of the nucleus globally and molecularly is to find ways that can faithfully preserve native nuclear interactions and enable subsequent detection of these interactions locally and with molecular precision. Most current mapping technologies including HiC and TCC depend on formaldehyde cross-linking to capture DNA proximity information through covalently linked higher-order protein-DNA complexes. However, the molecular details of this process are poorly defined. For example, there is no evidence that DNA-bound proteins can be stably and effectively cross-linked to DNA. In contrast, it seems that all formaldehyde based cross-linking technologies (ChIP or 3C-like approaches) for capturing protein-DNA complexes are actually the result of DNA being trapped in a higher-order protein-protein complexes cross-linked by formaldehyde. Thus the DNA proximity information captured by the current formaldehyde based methods may be biased the protein-protein complexes that are enriched and/or more formaldehyde reactive in certain regions of the nucleus. Formaldehyde cross-linking is a slow and difficult-to-control process, requiring tens of minutes to hours to generate significant protein-protein adducts at the working concentrations (1-4% v/v). Higher concentrations of formaldehyde lead to over fixing and difficulty in cell lysis. The slow reaction kinetics prevents dynamic analysis of the nuclear structure by the current methods, whereas the issue of over fixing limits the cross-linking efficiency.

Although some studies collected many more DNA-DNA proximity contacts by sequencing libraries prepared from large number of cells, this approach does not solve the observation-to-parameter issue because of the high heterogeneity of the chromosome conformations in the genomes of a population of cells. A related problem arising from the low data coverage is potential bias since particular regions of the genome may be more frequently sampled whereas other genomic regions may be missed. For determining the 3D structure of the genome the key is to detect as many as possible DNA-DNA proximity contacts per genome and sample the entire genome regions without bias. Because of the many limitations of formaldehyde cross-linking, improved methods are needed to capture nuclear interactions for structural analyses.

Figure 2:
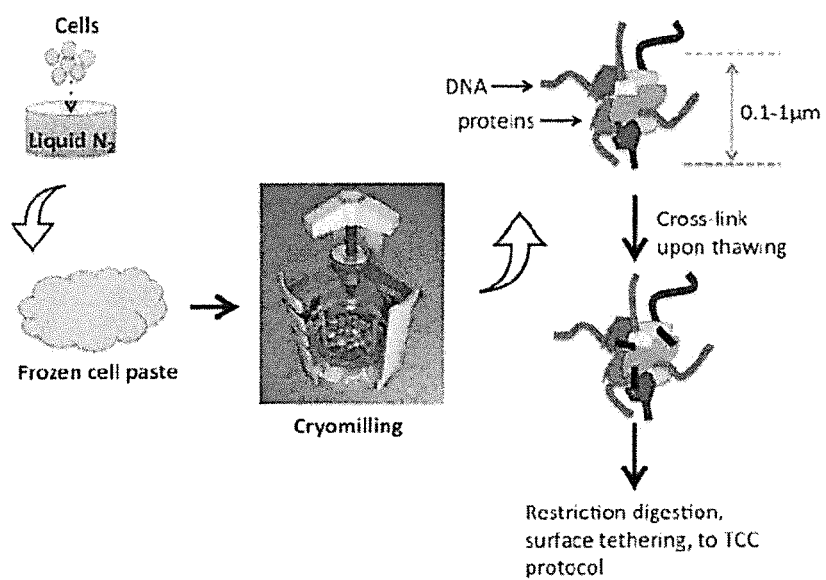
FIG. 2. The experimental work flow of the cryomilling-TCC protocol.

An attractive approach to capture the nuclear structure for molecular analyses is flash freezing/cryomilling. In brief, cells treated with proper cryopreserving buffers are rapidly frozen and the frozen cells are ground into small fragments under cryogenic conditions by mechanical forces (hence cryomilling). The resulting fragments, which range from sub-micrometer to tens of nanometers, presumably approach the size of macromolecular complexes of the cells (and the nucleus). These fragments, including the nuclear fragments, are analyzed by molecular and structural techniques directly or after chemical stabilization upon thawing. The inventors have adapted and optimized this technology for studying macromolecular complexes captured under native cellular conditions (refer to "Adapting Click DNA ligation to HiC/TCC analysis" section) (FIG. 2). Results demonstrated that the cyromilling approach can preserve complexes with ultra-fine structural details and can trap highly transient interactions. The inventors can use these established cryomilling approaches to study nuclear protein complexes and associated DNA-DNA contacts.

It is also recognized that cryomilling can be used to capture chromosome conformation for global, unbiased mapping of DNA-DNA proximities. This approach not only overcomes many limitations of formaldehyde mentioned but also provides additional advantages. These advantages include but are not limited to the following. First, the cells can be frozen and ground with high efficiency (99.95% cell lysis). Second, the cells can be flash frozen in sub-second time scale thus enabling dynamic analysis. Third, cryomilling breaks down the nucleus into small particles, which represent physical sampling of all nuclear regions. These particles can be much more effectively and equally accessed by enzymes and chemical reagents than the intact nucleus and chromatin, thereby enhancing efficiency and reducing bias. The particle size of cryomilling sets the sampling frequency and the resolution limit of structural analysis; it is the most critical technical parameter of this technology. The inventors, through intensive efforts and in collaboration with industrial developers, have successfully developed instruments and protocols that can reach particle size significantly less than 1 μm and possibly down to 100 nm. With a 100 nm-particle size, the nucleus of human cells (diameter ~10 μm) could be sampled in $10^6$ pieces, reaching a DNA resolution of about 3 kilobases (3 kb). Studies indicate that DNA in the ground nuclear particle is indeed close to the estimated range. Open access of the ground nuclear particles by enzymes can help reach the theoretical resolution limit set by the restriction enzyme cutting frequency (e.g., 256 bp for a 4 cutter).

The initial steps of chromosome capturing by formaldehyde cross-linking and cell lysis can be replaced by flash freezing and cryomilling. The basic steps of the cryomilling TCC, together with information to test and modify related experimental parameters are described below (FIG. 2):

1) Rapidly freeze cells treated with proper cryopreserving buffers in liquid nitrogen or other cryogenic medium using established procedures apparatus and procedures. Different cells can be tested for biological validation.

2) Cryomill cells into small particle of similar size. This is a critical step for applying cyromilling in TCC analysis. The inventors can cryomill cells into submicrometer size particle (<1 μm). It should be possible to reach a particle size of 100 nm, which may allow direct analysis of DNA fragments embedded in each particle to derive DNA-DNA proximity information. Different cells used the biological validation can be tested and it can be observed what particle size can be achieves. Regardless of the outcome, submicrometer size particles can be achieved routinely with any types of cells. One advantage of working with this medium size particle is that potential artifacts induced by excessive cyromilling can be avoided while greatly enhancing the accessibility of the cell particles by enzymes and reagents.

3) Thaw the ground particles in a cold (4° C.) lysis buffer in the presence of chemical cross-linking reagents (formaldehyde or glutaraldehyde). Compared with formaldehyde cross-linking of live cells, cross-linking of cryomilled cell particle is much more efficient and less prone to bias. Studies have shown that that brief (<60 seconds) treatment of cross-linking reagents at low concentration (0.1%) is sufficient to stabilize the particles without significant protein modifications. This is likely because only a small fraction of interacting proteins in the particle needs to cross-linked to maintain the structural integrity of the particle. Low level of protein modification also facilitates subsequence steps of the protocol, including protein modification for surface tethering and reversing cross-linking to release proteins before DNA extraction.

4) Stop cross-linking by centrifugation to separate the particles from the cross-linking solution. The chemically stabilized particles can be washed a few times and resuspended in a proper buffer for digestion by selected restriction enzymes. With cryomilling, the inventors can also avoid using detergent in cell lysis to minimize interference with enzyme digestion. Initial tests, for example, with HindIII and MobI, the two restriction enzymes used in our original TCC studies [Kalhor et al., NBT, 2012] can be performed, so that the inventors can compare the restriction enzyme digestion efficiency between the current and original protocols following our published procedures [Kalhor 2012]. With cryomilled nuclear particles, different enzyme concentrations and digestion times can be tested to optimize this step.

5) After DNA cutting, the restriction enzyme can be removed again by simple centrifugation. The resulting particles can be biotinylated via thiol (via Cys) and or amine (via Lys) specific conjugation reactions (see above). Subsequent steps of surface tethering, DNA ends joining and the enrichment and sequencing of DNA junctions can then follow the basic scheme of the core TCC protocol with improvements disclosed in the present invention.

Cryomilling is a significant improvement to the original TCC protocol. Rapid freezing enables dynamic analysis. Physical grinding ensures much less biased sampling of different nuclear regions. Easy access by enzymes and biochemical reagents to the ground nuclear fragments enhances data collecting efficiency. Many steps used in the original formaldehyde cross-linking protocol, such as sonication, heating and use of detergents, are no longer needed, thereby reducing potential artifacts associate with these steps. Most importantly, rapid freezing/cryomilling is a tried and true technology used by the inventors for studying protein complexes preserved under native cellular conditions. As described above, necessary modifications can be made, tested and optimized under a number of experimental parameters to adapt cryomilling to TCC analyses, using methods and reagents known to those of ordinary skill in the art. In fact, since rapid freezing and cyromilling can be generally applied with any types of cells, the cryomilling-TCC protocol is expected to be adapted by the broad research community for genome structural analysis.

Adapting Click DNA Ligation to HiC/TCC Analysis

In HiC/TCC and related technologies, a critical step is to generate, enrich and sequence DNA junctions from two DNA strands trapped in complexes captured by various techniques (see above). Currently this is done in at least two steps. The first is to fill in the restriction enzyme-generated DNA overhang by DNA polymerase (Klenow) to introduce a biotin-containing nucleotide analog (e.g., Biotin 14-dCTP, Invitrogen, Carlsbad, Calif.), which can be used to enrich DNA junctions in subsequent steps for high throughput sequencing. Second, the blunt end DNA molecules are ligated together by DNA ligases (e.g., T4 DNA Ligase). Studies with HiC and TCC indicate that this process very inefficient (estimated to be less than 5%), severely limiting the overall efficiency of the HiC and TCC protocol. This is probably due the intrinsically low efficiency of blunt-ended ligation and other factors, including non-optimal orientation of DNA ends in the captured complexes for ligation. Alternative approaches to join the DNA in order to overcome the present limitation of low ligation efficiency, and to expand the approach with new capabilities (e.g., to capture high-order DNA-DNA contact information located in the same captured chromatins or the sub-fragments) are described.

Figure 3:
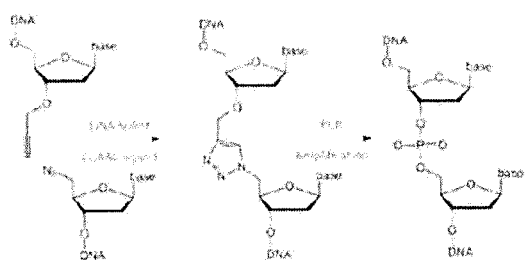
FIG. 3. Versatile Click DNA ligation. (a) 5' azide to 3' propargyl click ligation; (b) 3' azide to 5'-propargyl click ligation.
Figure 3:
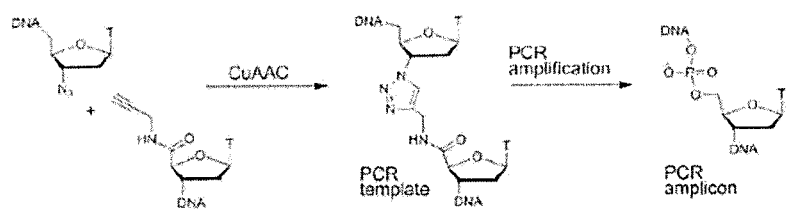
Figure 4:
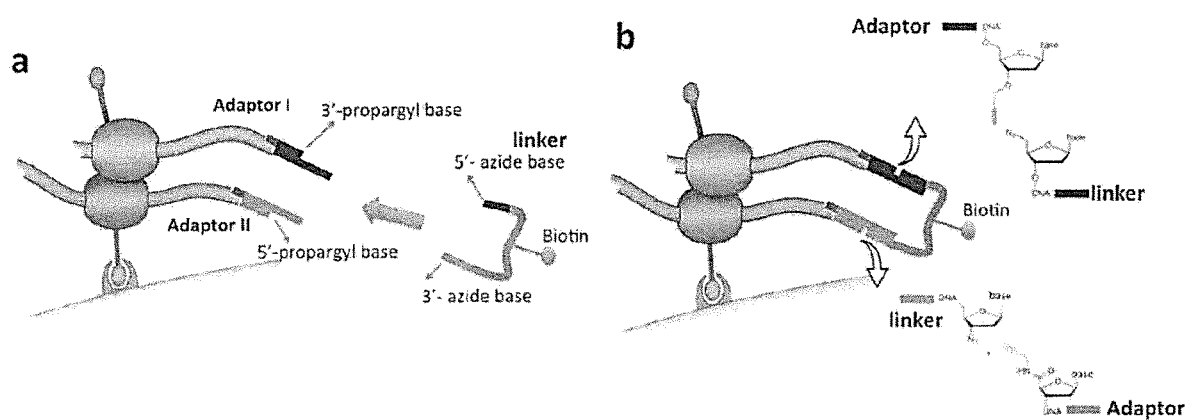
FIG. 4. Adapting Click DNA ligation to TCC analysis. (a) Schematic design of type I, type II adaptors and the linker; (b) click ligation reactions at the 5' and 3' end of the linker.

Given the rich nucleic acids chemistry that has been established for DNA/RNA synthesis and assembly, the inventors looked for chemical approaches that can join. DNA ends with high efficiency under conditions that are compatible with HiC and TCC and related approaches (single cell HiC or In Situ HiC etc.). After surveying a number of chemical approaches to DNA end joining, the inventors found that the approach based on the copper catalyzed azide-alkyne cycloaddition reaction, known as Click DNA/RNA Ligation, should work well. Click DNA ligation was originally developed for assembling large DNA molecules from short synthetic fragments (~150 bps), but the basic idea can be adapted for DNA end joining in HiC/TCC with some modifications. Click ligation is not only highly efficient, but also biocompatible in that the reaction can be carried out in in biological buffer solutions and that the ligated product can be amplified by PCR. Although certain junctions generated by click ligation may lead to one base deletion during PCR ligation, this has no consequence in the present invention. A variety of base analogs bearing the azide and propargyl groups at either the 5'- and 3'-end have been developed, some of which are commercially available from Glen Research (Sterling, Va., USA). If needed, other similar or different base analogs can be made in house using published procedures and knowledge of one of ordinary skill in the art. With different base analogs, click ligation can be performed in either directions of 5'-azide to 3'-propargyl or 3'-azide to 5'-propargyl (FIG. 3). As described below, this versatility of click ligation chemistry is critical for adaptation to TCC analysis. The basic idea to use click ligation with TCC is described in following steps (FIG. 4): (i) After digested protein-DNA complexes are immobilized on the surface, synthetic adaptors with sequence complementary to the restriction enzyme generated overhang on one end and base analogs carrying 5'- and 3'-propargyl groups on the other end can be ligated to the DNA ends. Two different adaptors are required to generate linked DNA that can be amplified by PCR. One (type I, blue in FIG. 4) has the 3'-propargyl group and extended, unique 5' sequence for linker docking and splint click 5'-azide/3'-propargyl click ligation. The other (type II, orange in FIG. 4) has the 5'-propargyl group and extended, unique 3' sequence for linker docking and splint click 3'-azide/5'-propargyl click ligation. One potential concern is that random distribution of the two different adaptors may limit the maximum efficiency to 50% because DNA ends with the same adaptors will not yield usable products. However, most of the captured complexes should have multiple DNA strands (FIG. 2) so the inventors are able to design the linker to have complementary sequences to the docking sequences of each adaptor such that the linker will always search for the correct pairs to generate PCR amplifiable products. (ii) After adaptor ligation, a synthetic linker carrying 5'- and 3'-azide groups can be added to capture the DNA ends through base pair docking. The inventors' design allows the use of excess amount of linker to maximally capture DNA ends without squelching because the linker won't self react, each of its ends can only react with one type of adaptor and that there are multiple DNA ends (hence adaptors) on one complex. (iii) After the excessive linker is washed away, the copper catalyst can be added to initiate the splint-mediated click ligation. The linker can also be designed to contain a biotin-bearing base analog for enriching and purifying the click ligation product, which can be processed following the TCC steps for sequencing (FIG. 1). The sequence of the linker can also be used as barcodes to capture high-order DNA-DNA contacts in the context of single cell HiC/TCC or a cryomilled nuclear fragment captured on a single bead. Each cell and particle can be processed by the above procedure using a linker with unique sequence. This could be done with the high throughput/multi-sample parallel processing platform developed by the inventors. After the click ligation, the cells and particles can be pooled together for combined processing and sequencing, and the barcode can be used to decipher the higher order DNA-DNA contact interaction. This represents a benefit in adapting click ligation to HiC/TCC analysis of genome conformation. Since the click ligation is applicable to RNA, the principle established in the present invention can also facilitate the analysis of RNA in genome. In sum, click ligation should have a big impact in improving the efficiency of HiC and TCC and enable a barcode strategy for analyzing the high-order chromatin contacts, which is a major breakthrough from the current methods that are limited to binary contacts. The higher-order DNA-DNA contacts should be useful in structure modeling given the complexity and heterogeneity of the genome, so that it can be determined if groups of contact occur in the same cells or in an ensemble of cells. Although single cell analysis does provide an answer to this question, the present invention should dramatically improve data collecting on single cell analysis. As described above, the core technology of click ligation has been well established and tested in many different systems. Its high efficiency and biocompatibility has been convincingly demonstrated in preliminary studies published in literature. Most of the regents required to synthesize the synthetic adaptors and linkers are commercially available and/or are known to one of ordinary skill in the art. It is also noted that splint click ligation step may also be carried out enzymatically. The versatility of click ligation allows engineering flexibilities for pursuing many other possible approaches. For example, base analogues carrying alkyne groups to fill in the overhang generated by restriction enzyme digestion could be used, followed by double click ligation using a linker that carries azide groups on both ends.

Photo Cross-Linking Technologies to Directly Probe DNA Proximity Information

Photo cross-linking technologies to directly probe DNA proximity information with high efficiency, regioselectivity, and temporal resolution are described. In human cells the 2 meter long genomic DNA (diameter 20 Å) is packed in the 10 μm-diameter nucleus, creating a crowded environment where the average distance between any two DNA segments is about 10 s A. While nuclear proteins such as histones facilitate close packing of the highly changed DNA polymer, many regions of the chromosomal DNA, including the outer face of the DNA in the nucleosome and the linker regions between nucleosomes, are accessible to small molecule binding. Thus, the close juxtaposition of DNA strands opens up the possibility to probe DNA-DNA proximities directly using cell permeable small molecules.

Figure 5:
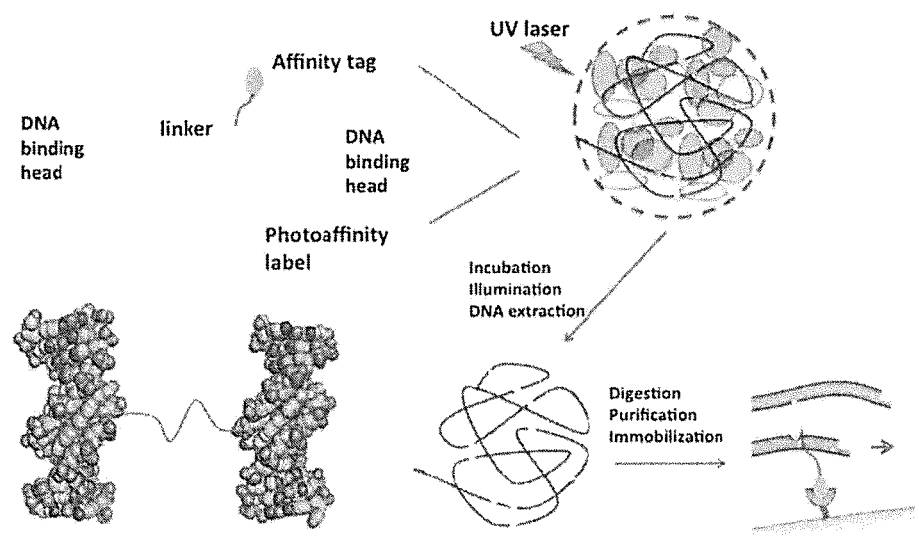
FIG. 5. Photo cross-linking to probe DNA-DNA proximity. General design of the probe. The work flow of the initial steps of the photochemical capturing protocol.

A series of bi-functional photo cross-linking probes that can bind and/or intercalate DNA at both ends, and under illumination by long wavelength UV or UV laser (e.g., 355 nm), form covalent adduct with DNA, thereby cross-linking two double stranded DNA in close spatial proximity together can be developed. The photo cross-linking probes should be cell permeable and bind DNA throughout the genome in live nucleus. It should have no or low cellular toxicity and should not significantly interfere with cellular/nuclear activities, at least during the short incubation time (for diffusion and binding). Many dye molecules used for nuclear staining of live cells meet these criteria. The photochemical cross-linking can be initiated at any given time point of interest. To achieve high temporal resolution, high UV laser coupled with selected photoaffinity labels that are highly reactive and can be activated by long wavelength UV can be used. The long UV wavelength is to minimize damaging nuclear proteins and DNA. The high intensity of UV laser and the high reactivity of photoaffinity label can ensure efficient cross-linking in seconds. This literally allows a UV picture of the DNA skeleton in the nucleus to be taken. Instead of chemically developing the traditional X-ray film, biochemical approaches can be used to extract structure information following the TCC protocols. Namely, after photo cross-linking, the cells can be lysed and the DNA can be extracted. This step should be much more efficient than formaldehyde cross-linked cells because the photo cross-linking probes are designed to only react with DNA (and RNA is they are nearby) in the nucleus. Moreover, because the DNA is already covalently linked together, not trapped by formaldehyde cross-linked protein complexes, the DNA extraction step can done with much harsher conditions to ensure maximum recovery. The extracted DNA can be digested by restriction enzyme. Again, the efficiency of this step should be greatly enhanced compared with formaldehyde cross-linking, because the recovered chromosomal DNA is fully naked and all the restriction sites throughout the genome should be equally accessible to the digestion enzymes, thereby reducing potential bias inherently associated with the original HiC/TCC protocols. After the digestion, the cross-linked DNA can be purified and immobilized on the tethering surface, and the DNA ends can be joined by the traditional enzymatic methods and/or the click DNA ligation described in the "Adapting Click DNA ligation to HiC/TCC analysis" section. The resulting DNA junctions can be recovered and sequenced following the rest steps of TCC described in FIG. 1. The design of bi-functional photo cross-linking probes can be explored using a protocol such as that described in FIG. 5. The inventors note that psoralen is known to bind mostly nucleosome free region, so the psoralen-based probe should target these regions. Compared with the non-specific cross-linking approaches, such as formaldehyde-crosslinking, which often produces DNA-DNA contacts that can be either of functional significances or contacts that are merely a consequence of the spatial confinement of the crowded genome DNA in the tight nuclear spaces (2 meter long DNA of 20 Å DNA in 10-20 μm diameter nuclear), psoralen targets nucleosome free regions, which are most likely the active regions that more likely engage in functional long rage interactions. In contrast, the nucleosome dense regions are mostly inactive genome regions that are more likely from local structures and their long, range contacts are most likely incidental. In any case, psoralen probes should be more selective in detecting contacts formed by active regions of the genome—transcription, recombination, and replications etc. This property can make psoralen an even more powerful probe to detect functionally meaningful chromatin contacts engaged by active regions, especially those long range and interchromosomal contacts. This approach can be expanded to psoralen, dye molecules that can be photocrosslinked to DNA and then enriched by click chemistry, if the probes can be coupled with laser with nm resolution and confocal resolution. Then any given regions in the cells can be illuminated and genome sequence in those regions can be identified with time and regional resolutions.

Figure 6A:
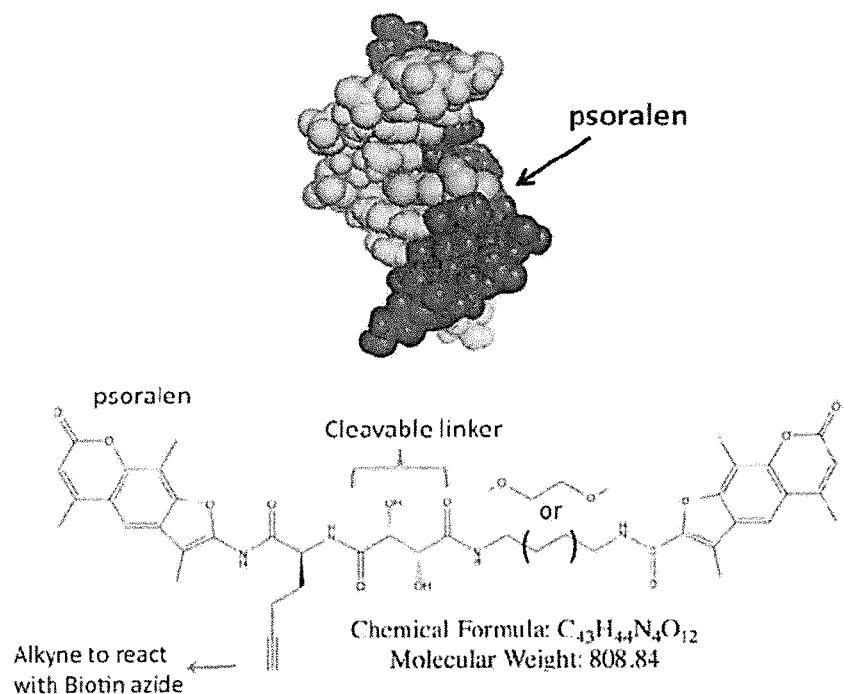
FIGS. 6a and 6b.
Figure 6B:
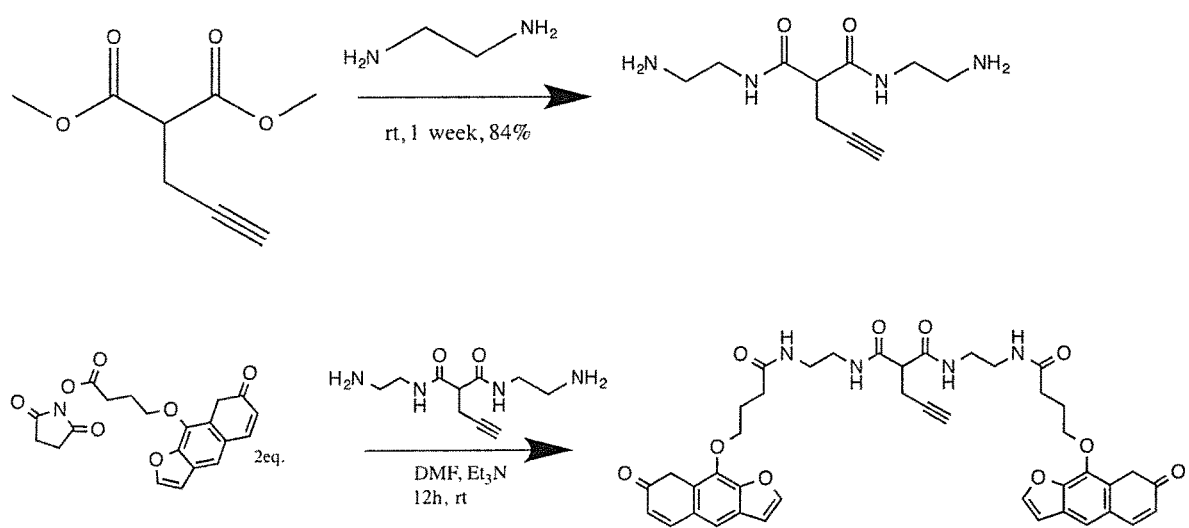

There are a variety of natural and man-made DNA-binding small molecules with good to excellent membrane permeability and cellular tolerance that can be used. Natural product psoralen and the synthetic dye 4',6-diamidino-2-phenylindole (a.k.a DAPI) can be tested. Both of these molecules have been extensively and successfully used in biochemical and in vivo studies of nucleic acid structures. One additional advantage of psoralen is its intrinsic ability to cross-link DNA/RNA under UV illumination (340-380 nm) with high yield (up to 80%). Despite being a natural product, psoralen can be readily modified by synthesis to make custom designed tools. The high-resolution structures of psoralen bound to DNA provide further guidance for the synthetic design (FIG. 6a, top). The inventors have designed a series of psoralen-based photo cross-liking probes for genome conformation capture, one of which is shown in FIG. 6a (bottom). Based on the crystal structure, the inventors chose exposed atoms of the bound psoralen as the linker positions, together with consideration of synthetic convenience. For the linker, the inventors introduced an alkyne for subsequent reaction with biotin-linked azide for purification of linked DNA. The inventors also introduced a cleavable linker for control experiments and for future use when it is desirable to cleave the link. The synthesis of one of the probe designed is described in FIG. 6b. Studies using this probe are described in FIGS. 8-11. For the initial method development, it is critical to determine if DNA junctions recovered by end joining (see FIG. 5, the last step) is indeed due to the linkage generated by the bifunctional photo cross-linking reaction. For this purpose, the inventors can take a fraction of the library, split equally into two halves. One half will go through the end joining as usual, while the other half will go through vicinal diol cleavage before the end joining procedure. Significantly lower recovery by the latter would support the potential role of bifunctional photo cross-linking in capturing DNA-DNA contacts, other results (similar or higher recovery by the latter) would signal potential problems.

Figure 7A:
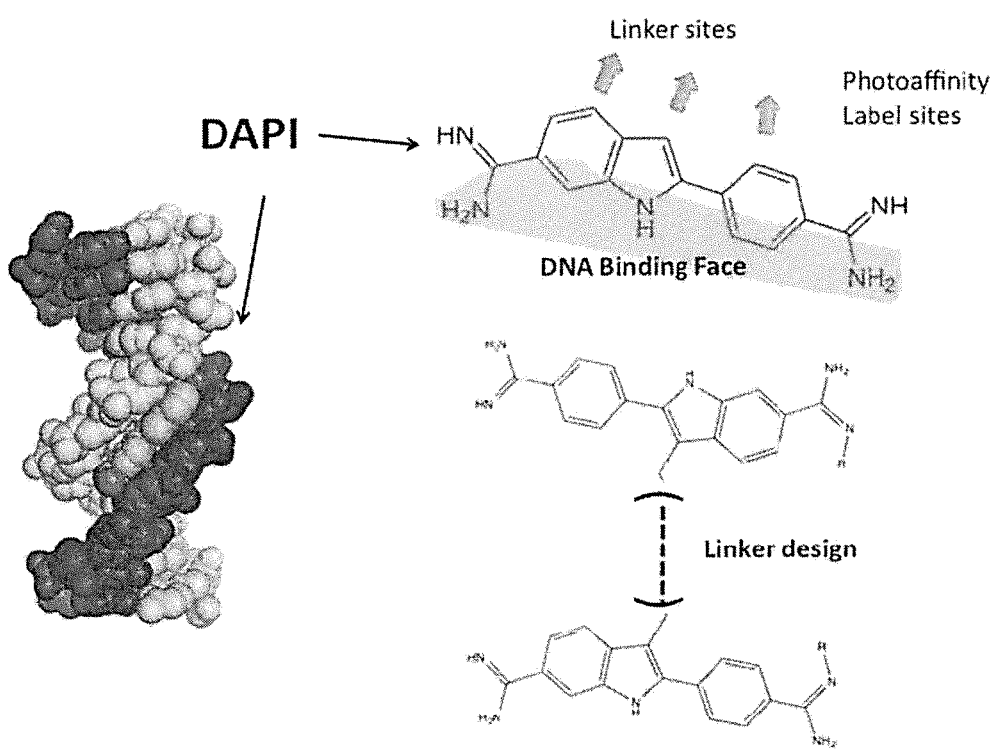
FIGS. 7a and 7b.

Using DAPI as the DNA binding head, the inventors have also designed a series of bifunctional DNA-DNA photo cross-linking probes. DAPI has very different DNA binding mode from psoralen and may therefore be used with the psoralen probes as a complementary pair of tools. Unlike psoralen that intercalates DNA between bases and undergoes 2+2 photoaddition upon UV illumination, DAPI wedges into the DNA minor groove and doesn't have intrinsic photochemical activity to cross-link with DNA. A photoaffinity label would therefore be introduced on DAPI. Again the crystal structure of DAPI bound to DNA can be used to guide this design. First, the DNA binding face of DAPI should be avoided in introducing photoaffinity labels and linker sites. Second, the photoaffinity label should be introduced at the sites that are near DNA for efficient cross-linking. Third, linker should be introduced at sites that point out and away from DNA. The general design scheme is shown in FIG. 7a. There are many possible photoaffinity labels, including benzophenone, arylazide, and diazirine. Diazirine is a choice because of its high stability in biochemical buffers, high cross-linking activity upon UV illumination and its long activation UV wavelength (330-370 nm). Many photo cross-linking studies in the literature report low capturing yields. This is often due to weak interaction between the photoaffinity probe and the target, so the highly reactive carbene (or nitrene) is quenched by buffer solution. The inventors have found that even with much less active photoaffinity probe such as bromo-dU (BrdU), a higher than 60% capturing yield can be achieved with most protein-DNA complexes when the BrdU is at or near the binding site. The tight binding of DAPI to DNA would also likely result in a high cross-linking yield by the introduced photoaffinity label (through the R group in FIG. 7a). An overall strategy and specific starting points for making a series of psoralen and DAPI based bi-functional DNA-DNA photo cross-linking probes is as follows.

Figure 7B:
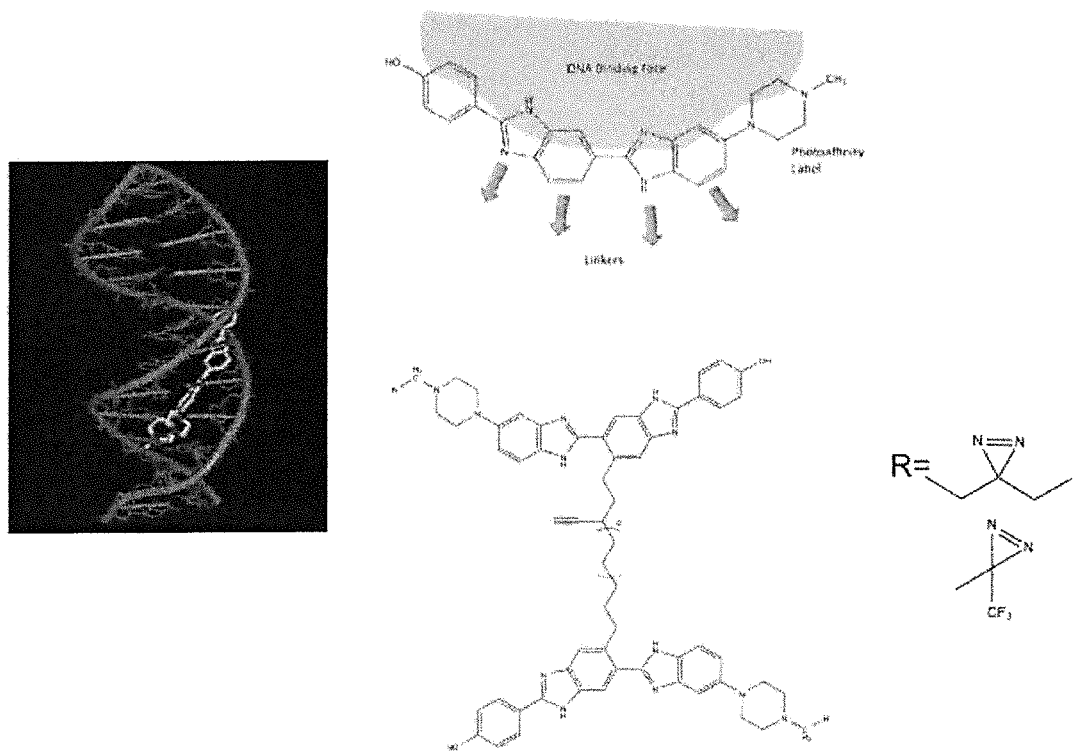
Figure 8:
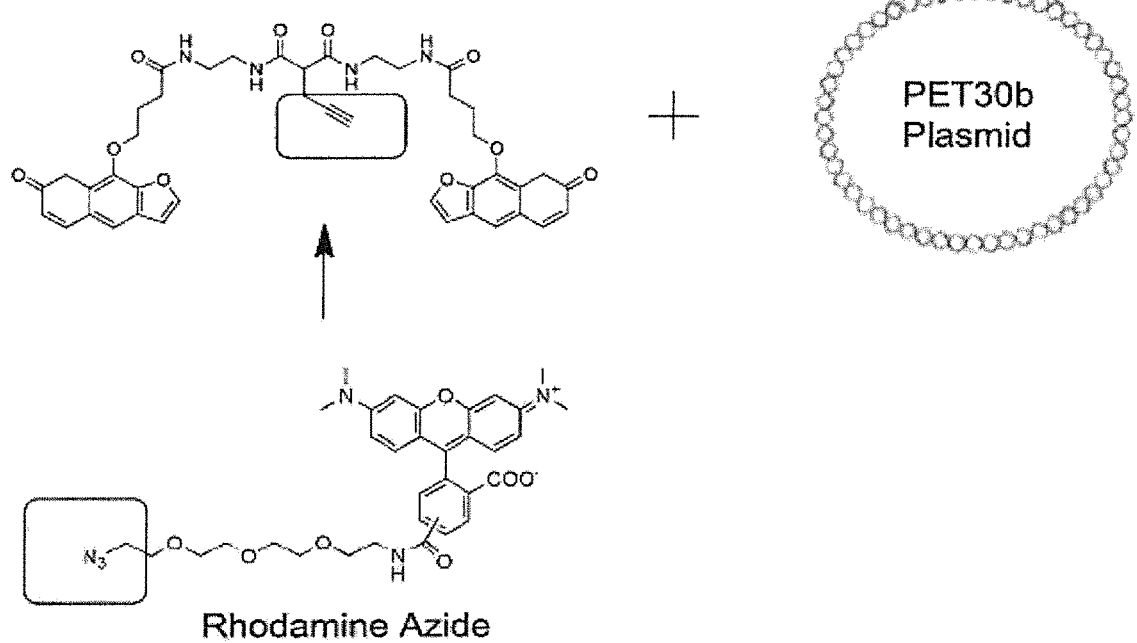
FIG. 8. The UV assisted photo crosslink feasibility was tested for the probe. Pet30b plasmid was used as DNA strand substrate with Rhodamine as indicator. The Rhodamine indicator has azide group that can react with alkyne affinity tag from the psoralen probe. The success of photo crosslink was shown by Rhodamine channel detection.
Figure 8:
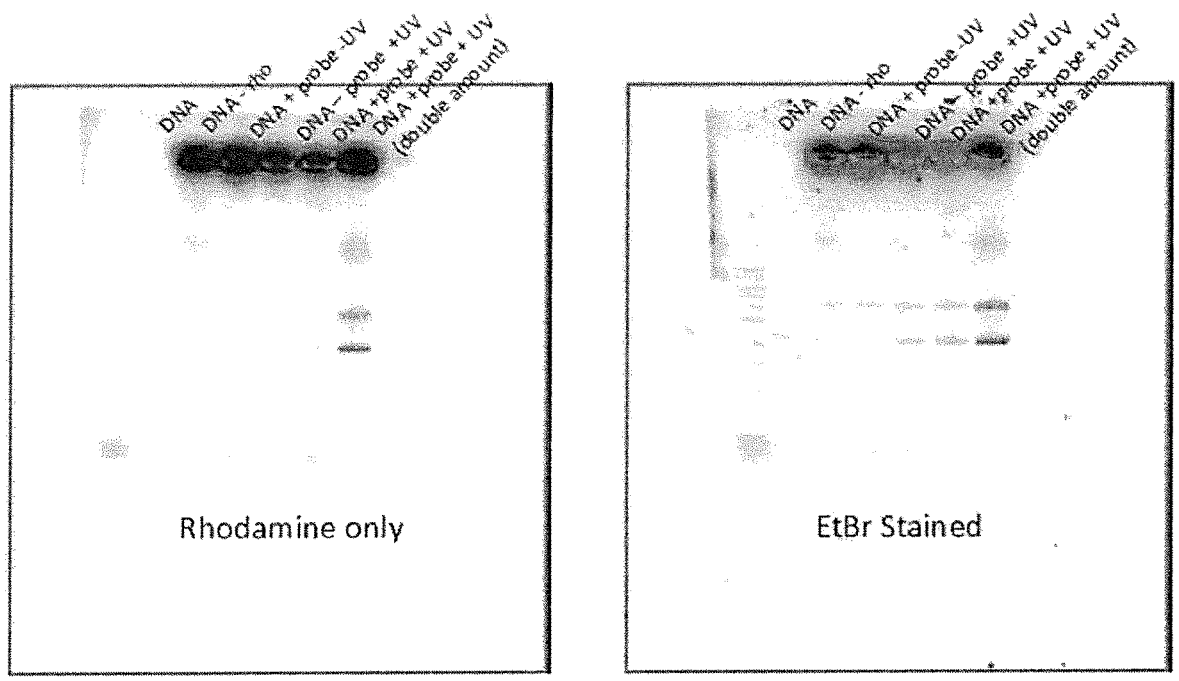
Figure 9:
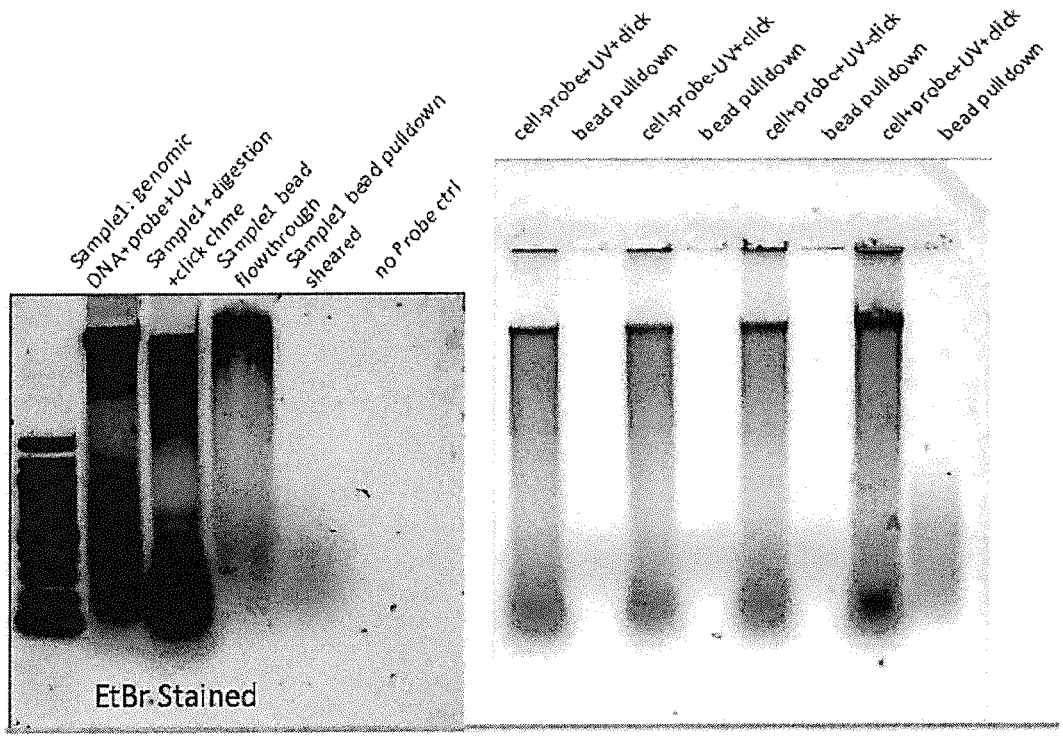
FIG. 9. Cell permeability enhancement and beads pull down test. To gain access into the cell while retaining the chromatin structure, permeation enhancement for fresh cell nuclei was tried based on established studies. The nuclear structure remains intact. To test the click chemistry success of the psoralen probe, the genomic DNA or the cell nuclei was incubated with probe, UV crosslinked, and clicked to biotin azide in order to be pulled down by the streptavidin beads. Probe presence, UV crosslink and click reactions are required for a successful beads pull down, which was confirmed by Covaris shearing shown in the gel.
Figure 9:
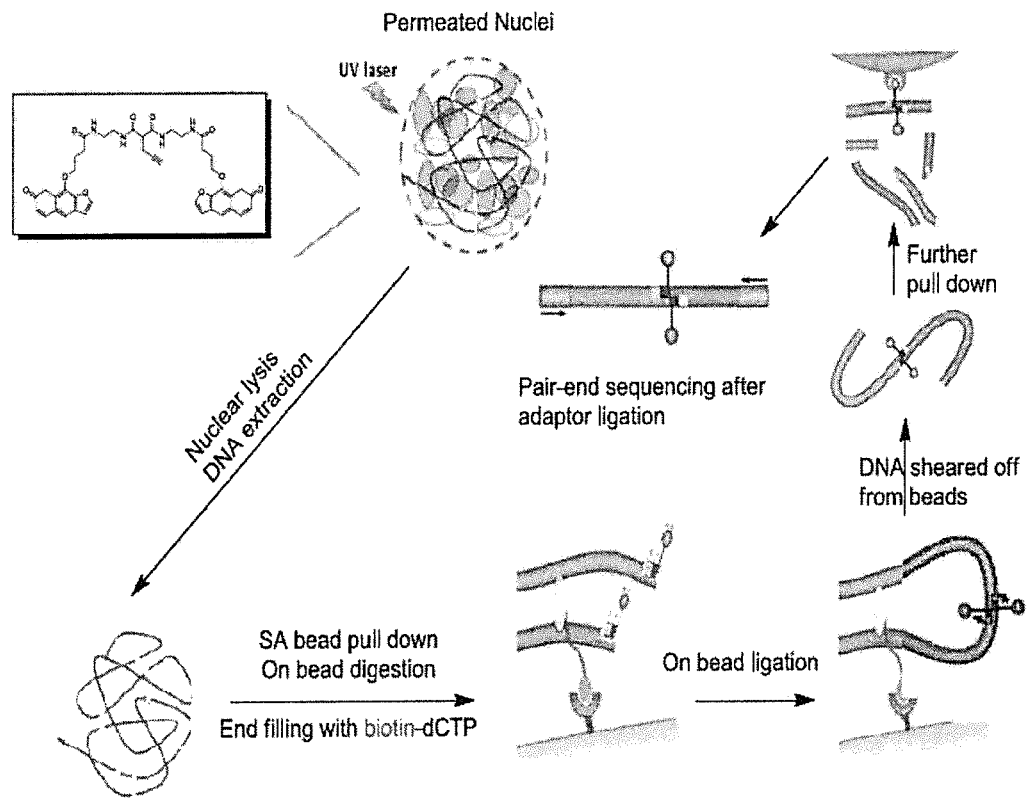
Figure 10:
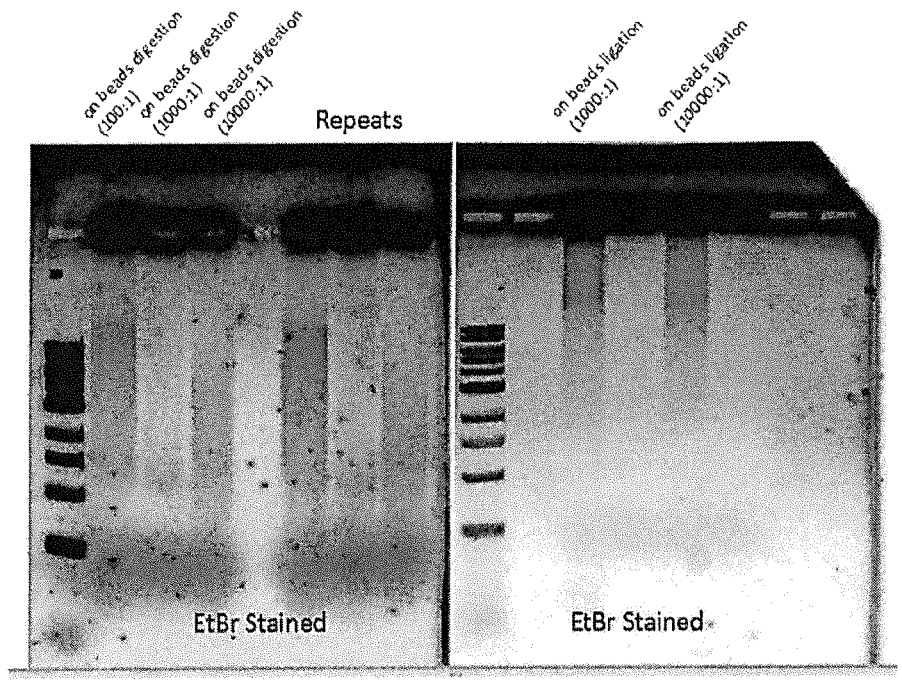
FIG. 10. On beads digestion and ligation confirmation. A major advantage of the current method over protein-based formaldehyde fixation is that the evaluation of chromatin contacts, particularly considering the restriction enzyme accessibility, can be processed outside the cell. The amount of probe used to cross-link genomic DNA can be optimized. Therefore, an on bead digestion with varying base pairs (bp): probe ratio was tested. The 10000:1 showed the most thorough cutting pattern. The afterwards on bead ligation showed larger band formation, indicating the success and the possibility for photo crosslink based tethered chromatin conformation capture.
Figure 10:
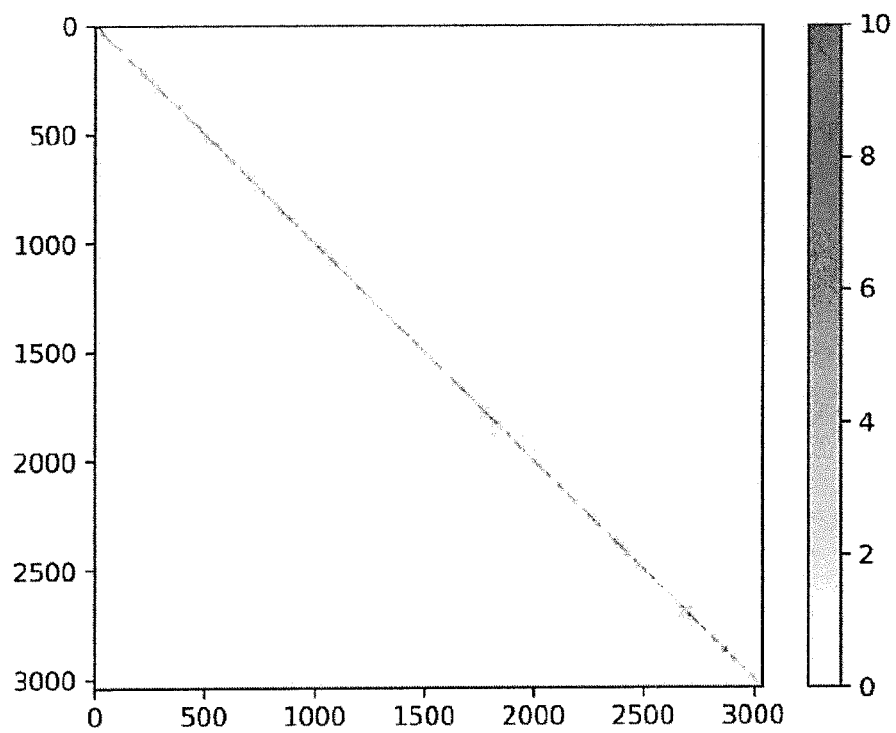

The design strategy described for DAPI can also be extended to other DNA binding molecules, including polyamides and other DNA staining dyes. For example, Hoechst 33258 can be used as the DNA binding head. As disclosed in FIG. 7b, the structure of Hoechst 33258 bound to DNA can be used to guide the design. For example, the DNA binding face of Hoechst 33258 should be avoided in introducing photoaffinity labels and linker sites. In addition, the photoaffinity labeling groups should be introduced at the sites of Hoechst 33258 that are near DNA for efficient cross-linking. And the linker should be introduced at Hoechst 33258 positions that point out and away from DNA.

The linker can be designed and tested with several considerations. First, different types (e.g., simple alkane chain, polyethylene glycol-PEG etc.) and lengths can be tested to balance solubility and cell permeability. The design disclosed in FIG. 6 should not have cell permeability issues given the modest molecular weight (~800 g/mol) and the excellent membrane permeability of psoralen. However, this is an important factor to keep in mind when designing longer or more complex linkers. Second, with the condition to maintain cell permeability, various linker lengths can be tested to optimize the efficiency in capturing DNA-DNA contacts. In addition, different linker lengths can be analyzed through computational modeling to determine if different structural information is captured at different length scales. Third, the rigidity of the linker can also be modified (e.g., by introducing double or triple bounds). One concern about the bifunctional photo cross-linking probes is that both DNA binding head may bind to the same DNA strands. Inventors believe that it is unlikely for the psoralen probes because psoralen intercalation induces DNA distortion in the nearby regions that disfavor an adjacent intercalation event. For the DAPI-based probes, this is also a low probability event for linkers less than 30 Å due to steric consideration. DAPI binds DNA minor groove in a specific wedging mode, modeling suggest that it would be energetically unfavorable for the second DAPI head to fold back and bind the adjacent minor groove unless the linker is very long, which the inventors will avoid. Most likely, the second DAPI head would search for nearby space for any DNA minor in this range to bind. This binding mode should be similar to the DNA bridging mode by the domain swapped FOXP3 dimer, which cannot bind adjacent sites on the same DNA, but rather bridge two DNA strands side-by-side. It is possible that some local DNA loops may be cross-linked by probes, while these local loops represent interesting information for high resolution analysis, they would be missed by the current analyses that can only sample at the restriction enzyme cutting frequency (for a 4 cutter, 256 bps). These local double cross-linking products can be estimated by the control experiments described above, namely by comparing the DNA junction recovery yields with and without the cleaving the vicinal diol linkage.

It is expected that the Bi-functional DNA photo-cross-linking (BFDPC) technologies to have the following features for structural analyses of nuclear organization. First, these technologies should provide a highly efficient, alternative cross-linking method than formaldehyde. The efficiency should rival that of formaldehyde or may be even higher. Second, BFDPC crosslink DNA-DNA directly, so it should be free of bias induced by different cross-linking efficiency of different chromatin complexes with formaldehyde. Although BFDPC may have its own limitation in terms of potential bias, it should be helpful to have proximity information detected by two different and potentially complementary methods for structural analysis. Third, the cross-linking reaction can be initiated by pulse of UV laser with sub-second resolution, such that detailed temporal analysis of the dynamic changes of chromatin structures can be conducted. Finally, the laser can also be focused with approximately 10 nm resolution so a selected region of the nucleus (e.g., specific nuclear compartments) of a single cell can be focused on to induce photo cross-linking reactions. With this approach, and by coupling with appropriate image methods known to those of ordinary skill in the art, the genomic context of a given nuclear regions, compartments, higher-order complexes at a given time point of the cellular activities can be selectively analyzed. With enhanced cross-linked efficiency and selected genomic regions, the inventors have a favorable observation-to-parameter ratio to refine high-resolution structure or achieve accurate dynamic information for a selected nuclear region of interest. Thus the present invention should helpful to derive specific biological insights that can help understand the structure-function relationship of the genome organization.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

The following references, patents and patent application publications, in addition to all references, patents and patent application publications listed in the specification and Exhibit A, are each relied upon and incorporated herein in their entirety.

WO 2011/146056
U.S. Pat. No. 8,076,070
Cremer, T., Cremer, M., Dietzel, S., Muller, S., Solovei, I., and Fakan, S. (2006). Chromosome territories—a functional nuclear landscape. Current opinion in cell biology 18, 307-316.
Dekker, J., Rippe, K., Dekker, M., and Kleckner, N. (2002). Capturing chromosome conformation. Science (New York, N.Y. 295, 1306-1311.
Dostie, J., Richmond, T. A., Arnaout, R. A., Selzer, R. R., Lee, W. L., Honan, T. A., Rubio, E. D., Krumm, A., Lamb, J., Nusbaum, C., et al. (2006). Chromosome Conformation Capture Carbon Copy (5C): a massively parallel solution for mapping interactions between genomic elements. Genome research 16, 1299-1309.
Wolffe, A. (1998). Chromatin: Structure and Function. Academic Press San Diego, Calif.
Cremer T., Cremer C. (2001). Chromosome territories, nuclear architecture and gene regulation in mammalian cells. Nat Rev Genet 4, 292-301.
Osborne, C. S., Chakalova, L., Brown, K. E., Carter, D., Horton, A., Debrand, E., Goyenechea, B., Mitchell, J. A., et al. (2004). Active genes dynamically colocalize to shared sites of ongoing transcription. Nature genetics 36, 1065-1071.
Lee, G. R., Spilianakis, C. G., and Flavell, R. A. (2005). Hypersensitive site 7 of the TH2 locus control region is essential for expressing TH2 cytokine genes and for long-range intrachromosomal interactions. Nature immunology 6, 42-48.
Spilianakis, C. G., and Flavell, R. A. (2004). Long-range intrachromosomal interactions in the T helper type 2 cytokine locus. Nature immunology 5, 1017-1027.
Cai, S., Lee, C. C., and Kohwi-Shigematsu, T. (2006). SATB1 packages densely looped, transcriptionally active chromatin for coordinated expression of cytokine genes. Nature genetics 38, 1278-1288.
Simonis, M., Klous, P., Splinter, E., Moshkin, Y., Willemsen, R., de Wit, E., van Steensel, B., and de Laat, W. (2006). Nuclear organization of active and inactive chromatin domains uncovered by chromosome conformation capture-on-chip (4C). Nature genetics 38, 1348-1354.
Zhao, Z., Tavoosidana, G., Sjolinder, M., Gondor, A., Mariano, P., Wang, S., Kanduri, C., Lezcano, M., Sandhu, K. S.
Lieberman-Aiden E, van Berkum N L, Williams L, Imakaev M, Ragoczy T, Telling A, Amit I, Lajoie B R, Sabo P J, Dorschner M O, Sandstrom R, Bernstein B, Bender M A, Groudine M, Gnirke A, Stamatoyannopoulos J, Mirny L A, Lander E S, Dekker J. (2009).
Science 1998; Apr. 24; 280(5363):547-53.
Science 2002; 295(5558):1306-11.
Spilianakis C G et al. Nature 2005; 435(7042):637-45.
Dostie J et al. Genome Res. 2006; 16(10):1299-309.
Simonis M et al. Nat Genet. 2006; 38(11):1348-54.
Zhao Z et al. Nat Genet. 2006; 38(11):1341-7.
Methods Enzymol. 2004; 375:493-507.
Methods Enzymol. 1987; 152:91-94.
Methods Enzymol. 1987; 152:33-41.

What is claimed is:

1. A method of determining DNA proximity information in a cell comprising:
   incubating the cell with a bi-functional DNA photo cross-linking probe;
   illuminating the cell with a long wavelength UV light or with a UV laser to produce photo cross-linked DNA:DNA complexes;
   extracting the photo cross-linked DNA:DNA complexes;
   digesting the extracted photo cross-linked DNA:DNA complexes;
   connecting the ends of the digested cross-linked DNA:DNA complexes by copper catalyzed azide-alkyne cycloaddition (Click) DNA ligation; and
   identifying proximity between DNA.

2. The method of claim 1, further comprising permeabilizing the cell before incubating the cell with the bi-functional DNA photo cross-linking probe.

3. The method of claim 1, wherein the bi-functional DNA photo cross-linking probe binds and/or intercalates DNA, and under UV illumination forms covalent adduct with DNA.

4. The method of claim 1, wherein the bi-functional DNA photo cross-linking probe comprises a dye and a linker.

5. The method of claim 4, wherein the dye is selected from the group consisting of psoralen, Hoechst 33258, 4'-6-diaminido-2-phenylindole (DAPI), a polyamide, and a combination thereof.

6. The method of claim 4, wherein the linker comprises an alkyne group.

7. The method of claim 4, wherein the linker is an alkane chain or a polyethylene glycol (PEG) linker.

8. The method of claim 4, wherein the bi-functional DNA photo cross-linking probe further comprises a photo affinity label and wherein the photo affinity label is benzophenone, arylazide or diazirine.

9. The method of claim 1, wherein the bi-functional DNA photo cross-linking probe is selected from the group consisting of:

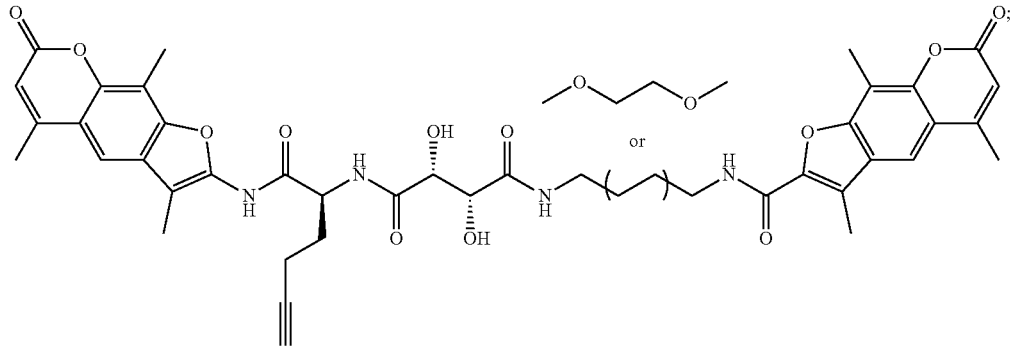

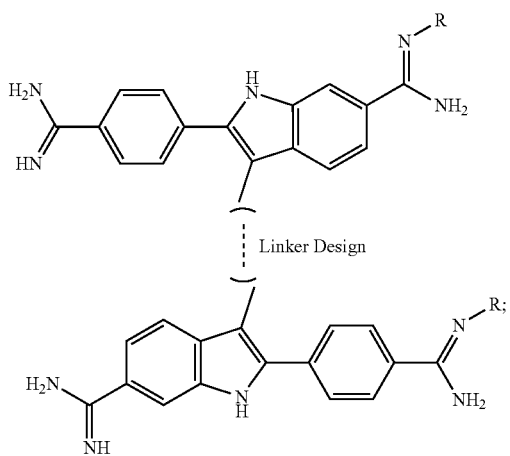

10. The method of claim 1, wherein extracting the photo cross-linked DNA:DNA complexes comprises lysing the cell by contacting the cell with sodium dodecyl sulfate.

11. The method of claim 1, wherein connecting the photo cross-linked DNA:DNA complexes ends by Click DNA ligation comprises contacting the digested photo cross-linked DNA:DNA complexes with biotin-linked azide to generate biotin-azide photo cross-linked DNA:DNA complexes, wherein the biotin-linked azide reacts with an alkyne group of the bi-functional DNA cross-linking probe.

12. The method of claim 11, further comprising contacting the biotin-azide photo cross-linked DNA:DNA complexes with magnetic beads coated with streptavidin to purify biotin-azide photo cross-linked DNA:DNA complexes.

13. The method of claim 1, further comprising sequencing the ligated photo cross-linked DNA:DNA complexes.

14. The method of claim 13, wherein sequencing is by massively parallel sequencing or ultrahigh-throughput sequencing.

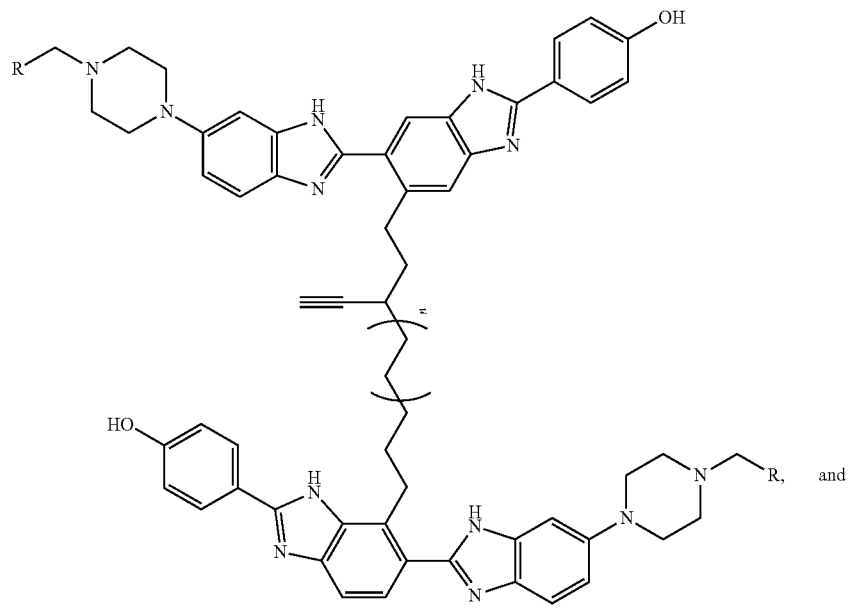

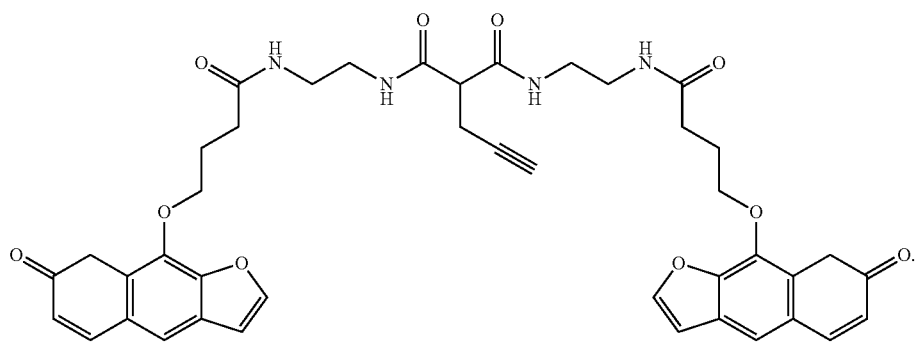 [SMILES: C#CCC(C(=O)NCCNC(=O)CCCOc1c2c(cc3ccoc13)C=CC(=O)C2)C(=O)NCCNC(=O)CCCOc1c2c(cc3ccoc13)C=CC(=O)C2]

15. A method of purifying complexes of DNA molecules in spatial proximity in a cell comprising:
- incubating the cell with a bi-functional DNA photo cross-linking probe;
- illuminating the cell with a long wavelength UV light or with a UV laser to produce photo cross-linked DNA:DNA complexes;
- extracting the photo cross-linked DNA:DNA complexes;
- digesting the extracted photo cross-linked DNA:DNA complexes;
- connecting the ends of the digested photo cross-linked DNA:DNA complexes by copper catalyzed azide-alkyne cycloaddition (Click) DNA ligation; and
- purifying ligated photo cross-linked DNA:DNA complexes.

* * * * *

UNITED STATES PATENT AND TRADEMARK OFFICE
CERTIFICATE OF CORRECTION

PATENT NO. : 11,359,227 B2  
APPLICATION NO. : 16/467941  
DATED : June 14, 2022  
INVENTOR(S) : Lin Chen Page 1 of 1

It is certified that error appears in the above-identified patent and that said Letters Patent is hereby corrected as shown below:

In the Specification

Column 1, Lines 19-22 read:
"This invention was made with government support under Grant Nos. R01 GM064642, R01 AI113009-01 A1 and 5U54 DK107981 awarded by the National Institutes of Health. The government has certain rights in the invention."

Should read:
--This invention was made with government support under AI113009, R01 GM064642, and DK107981 awarded by the National Institutes of Health. The government has certain rights in the invention.--

Signed and Sealed this
Fourth Day of October, 2022

Katherine Kelly Vidal
*Director of the United States Patent and Trademark Office*